United States Patent
Yomtov et al.

(10) Patent No.: US 7,599,737 B2
(45) Date of Patent: Oct. 6, 2009

(54) MEDICAL DEVICE FOR NEURAL STIMULATION AND CONTROLLED DRUG DELIVERY

(75) Inventors: Barry M. Yomtov, Marblehead, MA (US); Stephen J. Herman, Andover, MA (US); John T. Santini, Jr., North Chelmsford, MA (US)

(73) Assignee: MicroCHIPS, Inc., Bedford, MA (US)

( * ) Notice: Subject to any disclaimer, the term of this patent is extended or adjusted under 35 U.S.C. 154(b) by 315 days.

(21) Appl. No.: 10/679,763

(22) Filed: Oct. 6, 2003

(65) Prior Publication Data
US 2004/0127942 A1 Jul. 1, 2004

Related U.S. Application Data

(60) Provisional application No. 60/416,010, filed on Oct. 4, 2002.

(51) Int. Cl.
*A61N 1/00* (2006.01)
(52) U.S. Cl. .......................... 607/3; 604/890.1
(58) Field of Classification Search ............ 607/3, 607/41, 45, 48, 62, 52; 604/20–21, 65–67, 604/93.01, 890.1, 891.1, 892.1
See application file for complete search history.

(56) References Cited

U.S. PATENT DOCUMENTS

| | | | |
|---|---|---|---|
| 4,360,019 | A | 11/1982 | Portner et al. |
| 4,731,051 | A | 3/1988 | Fischell |
| 5,041,107 | A | 8/1991 | Heil, Jr. |
| 5,167,625 | A | 12/1992 | Jacobsen et al. |
| 5,200,051 | A | 4/1993 | Cozzette et al. |
| 5,252,294 | A | 10/1993 | Kroy et al. |

(Continued)

FOREIGN PATENT DOCUMENTS

DE 197 16 683 C1 6/1998

(Continued)

OTHER PUBLICATIONS

Bae, et al., "Pulsatile Drug Release by Electric Stimulus," ACS Symp. Series *Polymeric Drugs & Drug Admin.*, pp. 99-110 (1994).

(Continued)

*Primary Examiner*—Scott M Getzow
(74) *Attorney, Agent, or Firm*—Sutherland Asbill & Brennan LLP (57) ABSTRACT

Medical devices and methods are provided for electrical stimulation of neural tissue and controlled drug delivery to a patient. The device includes an implantable drug delivery module which comprises a plurality of reservoirs, a release system comprising at least one drug contained in each of the reservoirs, and control means for selectively releasing a pharmaceutically effective amount of drug from each reservoir; a neural electrical stimulator which comprises a signal generator connected to at least one stimulation electrode for operable engagement with a neural tissue of the patient; and at least one microcontroller for controlling operational interaction of the drug delivery module and the neural electrical stimulator. The microcontroller may control the signal generator and the control means of the drug delivery module. The device may further include a sensor operable to deliver a signal to the microcontroller, for example to indicate when to deliver electrical stimulation, drug, or both.

37 Claims, 4 Drawing Sheets

U.S. PATENT DOCUMENTS

| | | | |
|---|---|---|---|
| 5,324,316 A | 6/1994 | Schulman et al. | |
| 5,366,454 A | 11/1994 | Currie et al. | |
| 5,368,588 A | 11/1994 | Bettinger | |
| 5,368,704 A | 11/1994 | Madou et al. | |
| 5,380,272 A | 1/1995 | Gross | |
| 5,493,177 A | 2/1996 | Muller et al. | |
| 5,504,026 A | 4/1996 | Kung | |
| 5,524,338 A | 6/1996 | Martyniuk et al. | |
| 5,662,689 A | 9/1997 | Elsberry et al. | |
| 5,797,898 A * | 8/1998 | Santini et al. | 604/890.1 |
| 5,807,397 A | 9/1998 | Barreras | |
| 5,949,187 A | 9/1999 | Xu et al. | |
| 5,971,931 A | 10/1999 | Raff | |
| 5,989,445 A | 11/1999 | Wise et al. | |
| 6,001,090 A | 12/1999 | Lenhart | |
| 6,051,017 A | 4/2000 | Loeb et al. | |
| 6,081,736 A | 6/2000 | Colvin et al. | |
| 6,114,658 A | 9/2000 | Roth et al. | |
| 6,123,861 A | 9/2000 | Santini, Jr. et al. | |
| 6,129,685 A | 10/2000 | Howard, III | |
| 6,161,047 A | 12/2000 | King et al. | |
| 6,178,349 B1 | 1/2001 | Kieval | |
| 6,185,455 B1 | 2/2001 | Loeb et al. | |
| 6,214,032 B1 | 4/2001 | Loeb et al. | |
| 6,243,608 B1 | 6/2001 | Pauly et al. | |
| 6,289,237 B1 | 9/2001 | Mickle et al. | |
| 6,319,241 B1 | 11/2001 | King et al. | |
| 6,334,859 B1 | 1/2002 | Richter | |
| 6,349,232 B1 * | 2/2002 | Gordon | 604/20 |
| 6,384,353 B1 | 5/2002 | Huang et al. | |
| 6,436,853 B2 | 8/2002 | Lin et al. | |
| 6,480,730 B2 | 11/2002 | Darrow et al. | |
| 6,491,666 B1 | 12/2002 | Santini, Jr. et al. | |
| 6,527,762 B1 | 3/2003 | Santini, Jr. et al. | |
| 6,537,256 B2 | 3/2003 | Santini, Jr. et al. | |
| 6,551,838 B2 | 4/2003 | Santini, Jr. et al. | |
| 6,571,125 B2 | 5/2003 | Thompson | |
| 6,587,719 B1 * | 7/2003 | Barrett et al. | 607/2 |
| 6,656,162 B2 | 12/2003 | Santini, Jr. et al. | |
| 6,666,821 B2 | 12/2003 | Keimel | |
| 6,669,683 B2 | 12/2003 | Santini, Jr. et al. | |
| 6,733,485 B1 | 5/2004 | Whitehurst et al. | |
| 6,757,560 B1 | 6/2004 | Fischer et al. | |
| 6,782,292 B2 | 8/2004 | Whitehurst | 607/45 |
| 6,908,770 B1 | 6/2005 | McDevitt et al. | |
| 6,941,171 B2 * | 9/2005 | Mann et al. | 607/39 |
| 6,950,707 B2 * | 9/2005 | Whitehurst | 607/58 |
| 6,968,743 B2 | 11/2005 | Rich et al. | |
| 6,970,741 B1 * | 11/2005 | Whitehurst et al. | 607/3 |
| 7,010,345 B2 | 3/2006 | Hill et al. | |
| 7,097,775 B2 * | 8/2006 | Greenberg et al. | 216/2 |
| 7,190,997 B1 * | 3/2007 | Darvish et al. | 607/3 |
| 2001/0053885 A1 | 12/2001 | Gielen et al. | |
| 2002/0038137 A1 | 3/2002 | Stein | |
| 2002/0055761 A1 * | 5/2002 | Mann et al. | 607/41 |
| 2002/0072784 A1 | 6/2002 | Sheppard, Jr. et al. | |
| 2002/0082665 A1 | 6/2002 | Haller et al. | |
| 2002/0099359 A1 | 7/2002 | Santini, Jr. et al. | |
| 2002/0107470 A1 | 8/2002 | Richards et al. | |
| 2002/0107553 A1 | 8/2002 | Hill et al. | |
| 2002/0111601 A1 * | 8/2002 | Thompson | 604/514 |
| 2002/0111658 A1 | 8/2002 | Greenberg et al. | |
| 2002/0138067 A1 | 9/2002 | Sheppard, Jr. et al. | |
| 2002/0143369 A1 | 10/2002 | Hill et al. | |
| 2002/0144548 A1 | 10/2002 | Cohn et al. | |
| 2002/0151776 A1 | 10/2002 | Shawgo et al. | |
| 2002/0165586 A1 | 11/2002 | Hill et al. | |
| 2002/0183721 A1 | 12/2002 | Santini, Jr. et al. | |
| 2002/0187260 A1 | 12/2002 | Sheppard, Jr. et al. | |
| 2002/0188282 A1 | 12/2002 | Greenberg | |
| 2003/0004549 A1 | 1/2003 | Hill et al. | |
| 2003/0010808 A1 | 1/2003 | Uhland et al. | |
| 2003/0036794 A1 | 2/2003 | Ragheb et al. | |
| 2004/0082937 A1 * | 4/2004 | Ausiello et al. | 604/891.1 |
| 2005/0100937 A1 | 5/2005 | Holmes | |

FOREIGN PATENT DOCUMENTS

| | | |
|---|---|---|
| WO | WO 01/28629 A1 | 4/2001 |
| WO | WO 01/37926 A1 | 5/2001 |
| WO | WO 02/056862 A2 | 7/2002 |

OTHER PUBLICATIONS

Haroun, et al., "Local Drug Delivery," *Curr. Opin. Oncol.* 12(3): 187-93 (2000) (abstract).

Liu, et al., "Applications of Microfabrication and Micromachining Techniques to Biotechnology," *Tibtech* 15: 213-16 (1997).

Santini, el al., "Microchips as Controlled Drug-Delivery Devices," *Angew Chem. Int. Ed. Engl.* 39(14): 2396-407 (2000).

Santini, et al., "Microchip Technology in Drug Delivery," *Ann. Med*, 32(6) 377-79 (2001).

Santini, et al., "A Controlled-Release Microchip," *Nature* 397(6717): 335-38 (1999).

Tao, et al., "Microfabricated Drug Delivery Systems: from Particles to Pores," *Adv. Drug Deliv. Res.* 55(3): 315-28 (2003).

\* cited by examiner

MEDICAL DEVICE FOR NEURAL STIMULATION AND CONTROLLED DRUG DELIVERY

CROSS-REFERENCE TO RELATED APPLICATIONS

Priority is claimed to U.S. Provisional Application No. 60/416,010, filed Oct. 4, 2002. The application is incorporated herein by reference.

BACKGROUND OF THE INVENTION

This invention is generally in the field of methods and devices for the delivery of electrical signals to neural tissues in a medical patient in combination with the delivery of one or more drugs to the patient.

Electrical signals from implanted pulse generators have been applied to neural tissues for the control of chronic pain or movement disorders. For example, the delivery of electrical stimulation to the nervous system using an implanted electrode has been found effective in the relief of chest pain, such as angina pectoris, that often accompanies myocardial ischemia. U.S. Pat. No. 5,058,584 to Bourgeois, for example, discloses a system and method for treating chest pain using electrical stimulation within the epidural space of the spinal cord. U.S. Pat. No. 6,058,331 to King discloses a system and method for treating ischemia by automatically adjusting electrical stimulation to the spinal cord, peripheral nerve, or neural tissue ganglia based on a sensed patient condition. U.S. Pat. No. 5,199,428 to Obel et al. discloses a system for stimulating the epidural space with continuous and/or phasic electrical pulses using an implanted pulse generator upon the detection of myocardial ischemia to decrease cardiac workload, and thus reduce cell death associated with the ischemic event. As another example, U.S. Pat. No. 5,824,021 to discloses a system and method for providing spinal cord stimulation to relieve angina, and for notifying the patient that an ischemic event is occurring.

Other publications disclose therapeutic strategies and devices for the delivery of drug by catheters in combination with the use of electrical stimulation. See, e.g., U.S. patent application No. 2002/0013612 A1, U.S. patent application No. 2002/0055761 A1, and U.S. patent application No. 2002/0107553 A1, all of which are incorporated herein by reference.

When applied to control pain, implanted neural stimulators use electrical pulses to block the transmission of pain-related signals through neural tissue. In many cases, however, the neural stimulation is not completely effective in controlling the pain. It would be desirable to provide methods and devices for enhancing the control of chronic pain. When applied to control movement, the implanted neural stimulators use electrical pulses to block the transmission of cortical signals associated with the onset of certain types of seizures or for the control of continuous involuntary movement disorders. It would be desirable to provide methods and devices for enhancing the control of movement disorders. It would also be desirable to provide new devices and methods for the controlled delivery of electrical stimulation in combination with drug delivery for a variety of therapeutic applications.

SUMMARY OF THE INVENTION

Medical devices and methods are provided for electrical stimulation of neural tissue and controlled drug delivery to a patient in need thereof.

In one aspect, the medical device includes an implantable drug delivery module which comprises a plurality of reservoirs, a release system contained in each of the reservoirs, wherein the release system comprises at least one drug, and a control means for selectively releasing a pharmaceutically effective amount of the drug from each of the reservoirs; a neural electrical stimulator which comprises a signal generator connected to at least one stimulation electrode for operable engagement with a neural tissue of a patient; and at least one microcontroller for controlling operational interaction of the drug delivery module and the neural electrical stimulator. In one embodiment, the microcontroller controls both the signal generator and the control means of the drug delivery module. In one embodiment, the device further includes one or more sensors operable to deliver a signal to the microcontroller. For example, the sensors can control release of the drug from the drug delivery module and control generation of an electrical current from the neural stimulator to neural tissue. The device can further include a power source, for example, to operate the microcontroller, neural electrical stimulator, drug delivery module, or sensor if included.

In one embodiment, the stimulation electrode is on an outer surface of a hermetically sealed encasement containing the drug delivery module and microcontroller. In another embodiment, the stimulation electrode extends a distance from a hermetically sealed encasement containing the drug delivery module and microcontroller. For example, a flexible catheter can connect the stimulation electrode to the encasement.

In one embodiment, the device further includes telemetry components in operable communication with the microcontroller. This could be used, for example, to allow one to reprogram the medical device during use (e.g., to adjust the drug dose and/or the neural stimulation operational parameters), or to communicate sensor readings or device functions (e.g., battery status) to the patient.

In one embodiment, the neural electrical stimulator is provided as a module separate from the drug delivery module. In one embodiment, the neural electrical stimulator module is implantable. In one embodiment, the drug delivery module is controlled by a telemetry or hard-wired signal from the stimulator module. In one embodiment, the device comprises two microcontrollers, one of which controls the stimulator module and the other which controls the drug delivery module.

In one embodiment, the drug delivery module comprises a microchip drug delivery device. In one embodiment, the control means for selectively releasing a pharmaceutically effective amount of the drug comprises a reservoir cap positioned over each reservoir and a means for actively disintegrating the reservoir cap. For example, the reservoir cap can comprise an electrically conductive material and the means for actively disintegrating the reservoir cap can comprise an input lead and an output lead each connected to the reservoir cap and a power source for delivering an effective amount of electrical current through the reservoir cap, via the input lead and output lead, to heat and rupture the reservoir cap to release the drug.

In another aspect, a method is provided for treating a patient comprising delivery of an electrical signal and at least one drug to the patient. In one embodiment, the method includes implanting into the patient the implantable drug delivery module of the medical device described above; bringing the stimulator electrode of the medical device into operable engagement with a neural tissue of the patient; activating the signal generator to deliver electrical stimulation from the stimulator electrode to the neural tissue of the patient; and releasing the drug from the reservoir into the patient. In one embodiment, the method further includes implanting the neural electrical stimulator into the patient. In various embodiments, the electrical stimulation is delivered intermittently or continuously.

In one embodiment, the drug and the electrical neural stimulation are delivered simultaneously. In another embodiment, release of the drug is alternated with delivery of the electrical stimulation. In various embodiments, the drug is delivered intermittently or continuously. In one embodiment, the drug is released before the electrical neural stimulation and is effective to reduce the stimulation threshold of the neural tissue.

In exemplary applications, the devices and methods are adapted for treating chronic pain, for treating a movement disorder, for treating incontinence, for treating obesity, or for controlling seizures in the patient. In various embodiments, the drug comprises an analgesic, an anti-anxiety agent, an anti-incontinence agent, a skeletal muscle relaxant, an anti-convulsant, or an anti-parkinson agent.

DESCRIPTION OF THE INVENTION

A medical device is provided for use in neural stimulation and the controlled delivery of one or more therapeutic or prophylactic drugs. The devices are useful for treating patients suffering from diseases and disorders that may be better treated or managed with a combination of electrical stimulation and drug therapy. For example, the drug may augment the stimulation therapy, it may negate a side effect of the stimulation therapy, or it may reduce the stimulation threshold in the treatment.

In one embodiment, the devices are used in the control of chronic pain. The devices advantageously can provide a more effective treatment with the combination than with either alone, for example, by alternating electrical stimulation and drug delivery in order to prevent a potential tolerance build-up to either therapeutic approach if used alone. This could extend the useful longevity of an implanted electrical stimulation device.

In another embodiment, the devices are used in the treatment of movement disorders, by blocking the transmission of cortical signals associated with the onset of certain types of seizures or for the control of continuous involuntary movement disorders. For example, this embodiment could be used in the treatment of epilepsy, Parkinson's disease, or spasticity. Advantageously, these devices could deliver a drug that reduces the stimulation threshold, thereby enabling a reduction in power requirements. This also could extend the device longevity, or could permit a smaller implant size than might otherwise be required (e.g., enabling the use of a smaller battery).

In still other embodiments, the therapeutic devices could be used in the treatment or control of incontinence, or mood and/or anxiety disorders.

As used herein, the terms "comprise," "comprising," "include," and "including" are intended to be open, non-limiting terms, unless the contrary is expressly indicated.

I. Device Components and Materials

Figure 1:
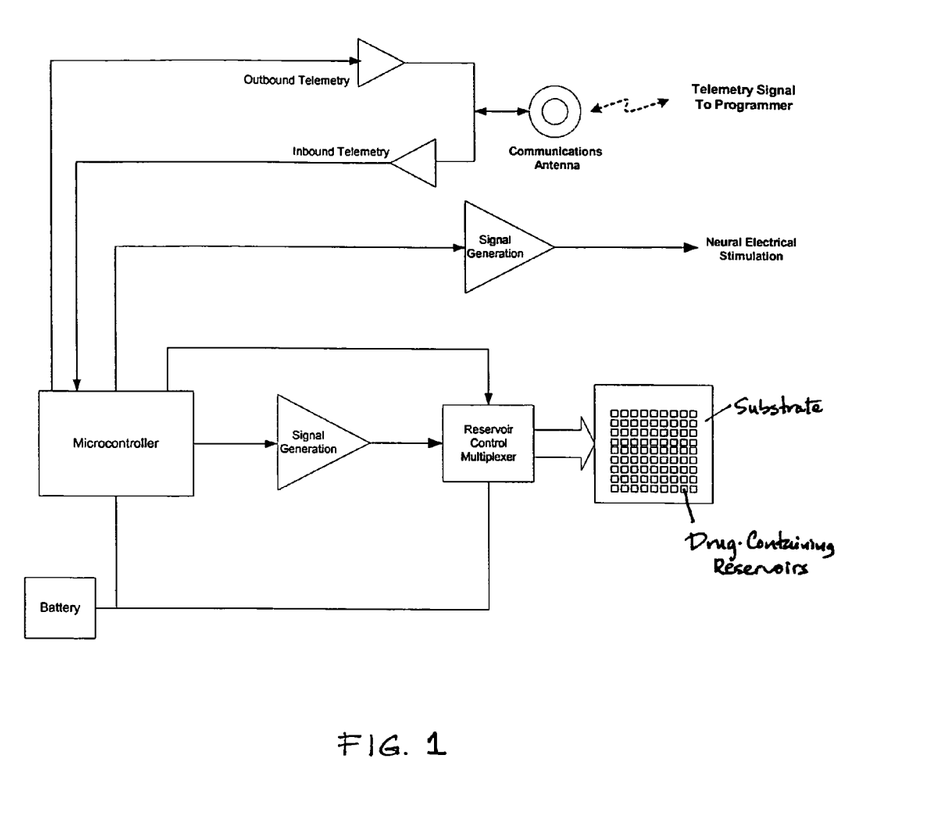
FIG. 1 is a schematic drawing of the components in one embodiment of the medical device described herein.

In one embodiment, the medical device includes (i) an implantable drug delivery module which comprises a plurality of reservoirs, a release system contained in each of the reservoirs, wherein the release system comprises at least one drug, and a control means for selectively releasing a pharmaceutically effective amount of the drug from each of the reservoirs; (ii) a neural electrical stimulator which comprises a signal generator connected to at least one stimulation electrode for operable engagement with a neural tissue of a patient; and (iii) at least one microcontroller for controlling operational interaction of the drug delivery module and the neural electrical stimulator, such as for controlling the signal generator and the control means of the drug delivery module. The device may further include a sensor operable to deliver a signal to the microcontroller, for example to indicate when to deliver electrical stimulation, drug, or both. One embodiment of the medical device is illustrated schematically in FIG. 1.

In one embodiment, the entire medical device is implanted into the body of the patient at a single location, such that the electrodes are mounted onto a surface of the packaged medical device.

Figure 2:
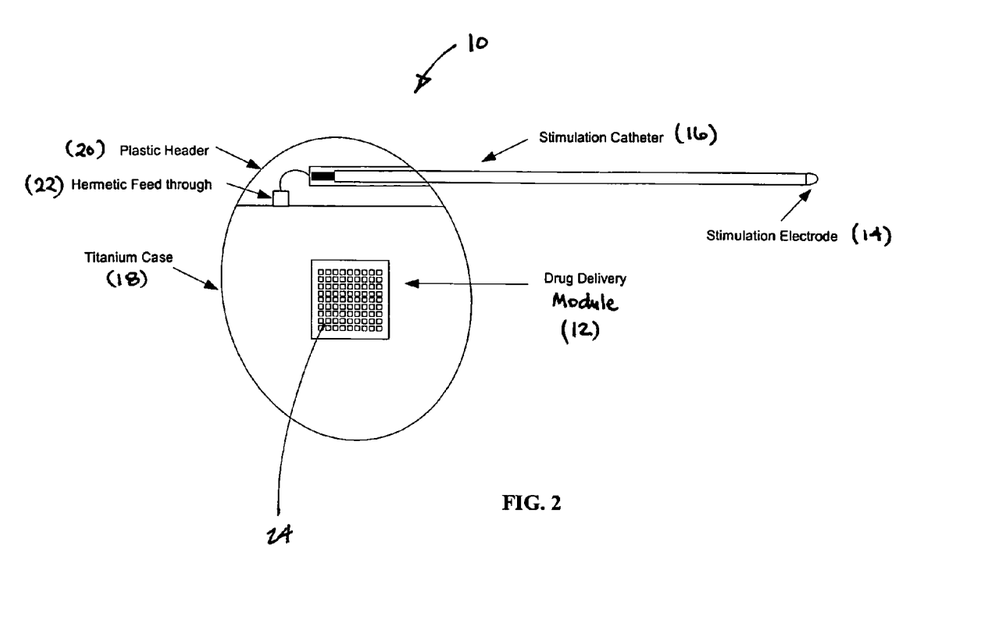
FIG. 2 is a plan view of one embodiment of a medical device comprising an implantable drug delivery module with a remote neural stimulation electrode.

In another embodiment, the drug delivery device is implanted at a first location and the electrodes extend to neural tissue at another location, such as with a catheter, which would be particularly useful to place the stimulation electrode in the epidural space of the spinal cord. One example is illustrated in FIG. 2. It shows implantable medical device 10 which includes drug delivery module 12 provided in titanium case 18. The drug delivery module 12 includes an exposed array of reservoir caps 24 which cover drug-containing reservoirs. The medical device 10 further includes a plastic header 20 connected to the titanium case 18. An electrical lead extends through hermetic feed through 22 in the header 20, into stimulation catheter 16, and connects to stimulation electrode 14.

Figure 3:
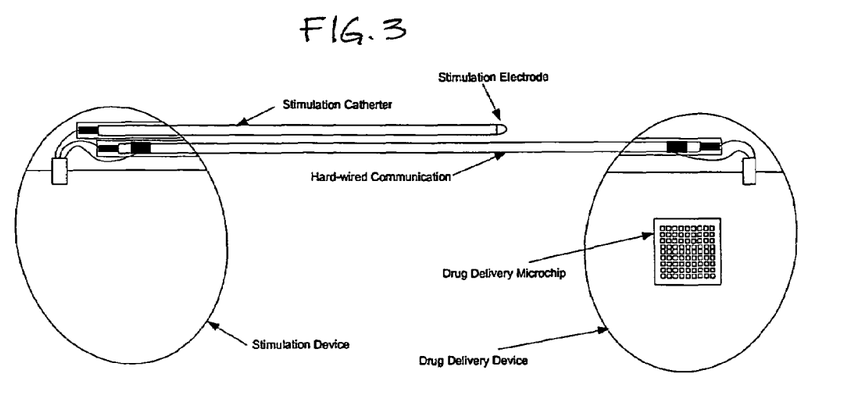
FIG. 3 is a plan view of one embodiment of a medical device comprising an implantable drug delivery module operably linked to a stimulation module by a hardwired communication link.
Figure 4:
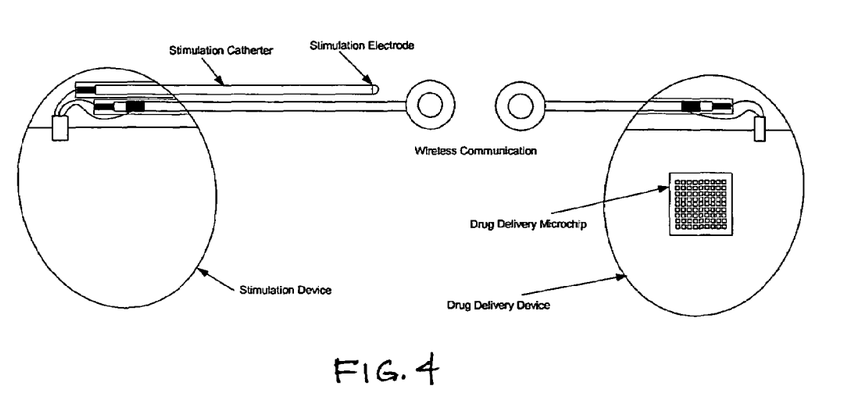
FIG. 4 is a plan view of one embodiment of a medical device comprising an implantable drug delivery module operably linked to a stimulation module by a wireless communication link.

In yet another embodiment, the drug delivery module is "free-standing" from the neural stimulator portion (i.e., the stimulator module) of the medical device. For example, the drug delivery module could be implanted and controlled by a telemetry or hard-wired signal from the stimulator module, as illustrated in FIG. 3 and FIG. 4. In such embodiments, there may be two microcontrollers: one for the stimulator module and one for the drug delivery module. In one embodiment, the two modules could "hand off" operation to each another at specified timed intervals, or upon patient activated events. For example, the medical device could further include a physiological sensor capable of detecting onset of a seizure (e.g. epilepsy), where the stimulation module delivers electrical stimulation to prevent or reduce the occurrence of seizures and the drug delivery module activates release of a drug if a seizure is detected. Alternatively, the operation of the two modules could occur simultaneously or in an overlapping manner. The stimulator module could be implanted and used in combination with a drug delivery module for pain control or motion control. When both modules are implanted separately, they can be replaced independently at the required intervals, e.g., the drug delivery module when the drugs have been expended and the stimulator when the battery fails.

A. The Electrical Stimulation Means

The stimulation module includes a signal generator connected to at least one stimulation electrode suitable for operable engagement with a neural tissue of a patient. The stimulation electrode is connected to a power source, such as a battery/pulse generator, which provides the energy/signal source for the stimulation. The stimulation is between a stimulation electrode (i.e., a cathode) and a return electrode (i.e., an anode), which could be either the case (i.e., packaging) of the medical device or a secondary remote electrode. The electrode may be either monopolar, bipolar, or multipolar.

The electrodes may come in a variety of forms or structures, depending on the particular application. Preferably, the electrode is a known type suitable for implantation within a patient, preferably for an extended period of time. The implantable electrode may be positioned at a location within a patient by any of a variety of conventional mechanisms (including mechanical or chemical means, and possibly relying on gravity and/or frictional forces). In one embodiment, conventional implantable electrodes may be surgically inserted into the spinal region adjacent the T1-T12 and C1-C8 vertebrae, and may be located near or even immediately adjacent the T1-T12 and C1-C8 nerve bundles for spinal cord stimulation.

Preferably, the stimulating electrical signal is operated at a voltage between about 0.1 $\mu V$ and about 20 V, more preferably between about 1 V to about 15 V. For microstimulation, it is preferable to stimulate within the range of 0.1 $\mu V$ and about 1 V. Generally, the electric signal source is operated at a frequency range between about 2 Hz and about 2500 Hz, preferably between about 2 Hz and about 200 Hz. The pulse width of the oscillating electrical signal can be between about 10 $\mu s$ and about 1,000 $\mu s$, preferably between about 50 $\mu s$ and about 500 $\mu s$.

The electrodes may be placed subcutaneously to stimulate underlying muscles, overlying cutaneous nerves, or passing somatic nerves. For example, peripheral nerve stimulation leads are available from Medtronic, Inc. (e.g., lead Model 3987, On Point™, which includes contacts and a polyester mesh skirt for fixation to subcutaneous tissue or muscle fascia; lead Model 3587A or Model 3998, which have an insulative paddle enlargement; or lead Model 3487A or Model 3888, which do not have an insulative paddle enlargement). In both surface mounted and implanted electrodes, electrical signals supplied by a microcontroller to the electrodes electrically stimulate nervous tissue in the spinal canal.

Implantable electrodes may be placed adjacent to nerves such as the median, peroneal, ulnar, and ansalenticularis nerves. Similarly, implantable electrodes may be placed near the vagus nerves, carotid sinus, and all other cranial nerves to provide stimulation. Finally, implantable electrodes may be placed epicardially or transvenously near the cardiac ganglia or plexi and employed in this manner. Some examples of commercially available electrode stimulator devices that could be adapted for use with the drug delivery devices described herein include the VNS (Vagus Nerve Stimulator) using a cuff type electrode made by Cyberonics, Inc. (Houston, Tex.), as well as certain electrodes/stimulators made by Medtronics, Inc. (Minneapolis, Minn.), which includes deep brain catheter leads/electrodes for use in some movement disorders/tremors.

In one embodiment, as described above, the stimulating electrode may be remote from the titanium case enclosure, as shown in FIG. 2.

B. The Controlled Drug Delivery Module

The drug delivery device includes a substrate having a plurality of reservoirs, which contain the drug molecules for delivery. In one embodiment, the drug delivery module comprises a microchip drug delivery device. The substrate, reservoirs, reservoir caps, control circuitry, and power source are described at least in pan herein and/or in U.S. Pat. No. 5,797,898, No. 6,123,861, No. 6,551,838, No. 6,491,666, and No. 6,527,762, as well as U.S. Patent Application Publications No. 2002/0138067, No. 2002/0072784, No. 2002/0151776, and No. 2002/0107470, in one embodiment, control of reservoir cap opening includes electro-thermal ablation techniques, as described in U.S. patent application Ser. No. 10/641,507, filed Aug. 15, 2003, published as U.S. Patent Publication No. 2004/0121486, which is incorporated herein by reference.

The Substrate and Reservoirs

The substrate is the structural body (e.g., part of a device) in which the reservoirs are formed, e.g., it contains the etched, machined, or molded reservoirs. A reservoir is a well, a container. MEMS methods, micromolding, and micromachining techniques known in the art can be used to fabricate the substrate/reservoirs from a variety of materials. See, for example, U.S. Pat. No. 6,123,861 and U.S. patent application Publication No. 2002/0107470. Examples of suitable substrate materials include metals, ceramics, semiconductors, and degradable and non-degradable polymers. The substrate, or portions thereof, may be coated, encapsulated, or otherwise contained in a biocompatible material. Examples of coating materials include poly(ethylene glycol), polytetrafluoroethylene-like materials, inert ceramics, titanium, diamond-like carbon, and the like. In one embodiment, the substrate is formed of silicon.

The substrate can be flexible or rigid. In one embodiment, the substrate serves as the support for a drug delivery microchip.

The substrate can have a variety of shapes, or shaped surfaces. It can, for example, have a release side (i.e., an area having reservoir caps) that is planar or curved. The substrate may, for example, be in a shape selected from disks, cylinders, or spheres. In one embodiment, the release side can be shaped to conform to a curved tissue surface or into a body lumen. In another embodiment, the back side (distal the release side) is shaped to conform to an attachment surface.

The substrate may consist of only one material, or may be a composite or multi-laminate material, that is, composed of several layers of the same or different substrate materials that are bonded together.

Preferably, the substrate is hermetic, that is impermeable (at least during the time of use of the reservoir device) to the molecules to be delivered and to surrounding gases or fluids (e.g., water, blood, electrolytes or other solutions).

In another embodiment, the substrate is made of a strong material that degrades or dissolves over a defined period of time into biocompatible components. Examples of biocompatible polymers include poly(lactic acid)s, poly(glycolic acid)s, and poly(lactic-co-glycolic acid)s, as well as degradable poly(anhydride-co-imides).

The substrate thickness can vary. For example, the thickness of a device may vary from approximately 10 $\mu m$ to several millimeters (e.g., 500 $\mu m$). Total substrate thickness and reservoir volume can be increased by bonding or attaching wafers or layers of substrate materials together. The device thickness may affect the volume of each reservoir and/or may affect the maximum number of reservoirs that can be incorporated onto a substrate. The size and number of substrates and reservoirs can be selected to accommodate the quantity and volume of drug formulation needed for a particular application, although other constraints such as manufacturing limitations or total device size limitations (e.g., for implantation into a patient) also may come into play. For example, devices for in vivo applications desirably would be small enough to be implanted using minimally invasive procedures.

The substrate includes at least two and preferably tens or hundreds of reservoirs. For example, one reservoir could be provided for each daily dose of drug required, for example, over a 3-, 8-, or 12-month course of treatment. The substrate could include, for example, 300 to 400 reservoirs.

In one embodiment, the reservoir has a volume equal to or less than 500 µL (e.g., less than 250 µL, less than 100 µL, less than 50 µL, less than 25 µL, less than 10 µL, etc.) and greater than about 1 nL (e.g., greater than 5 nL, greater than 10 nL, greater than about 25 nL, greater than about 50 nL, greater than about 1 µL, etc.).

Drug and Release System

The drug delivery device includes a single drug or a combination of two or more drugs for release. The drug can comprise small molecules, large (i.e., macro-) molecules, or a combination thereof, having a bioactive effect. In one embodiment, the large molecule drug is a protein or a peptide. In various embodiments, the drug can be selected from amino acids, nucleic acids, oligonucleotides, polysaccharides, and synthetic organic molecules. In one embodiment, the drug is selected from nucleosides, nucleotides, and analogs and conjugates thereof. Representative examples of drugs include analgesics, anesthetics, anti-angiogenic molecules, antibiotics, antibodies, antineoplastic agents, antioxidants, antiviral agents, chemotherapeutic agents, gene delivery vectors, immunomodulators, ion channel regulators, metabolites, sugars, psychotropic agents, vaccines, vitamins.

In one embodiment, the drug is used in the control of chronic pain. For example, the drug could be an analgesic, such as aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, fentanyl, or meprobamate.

In other embodiments, the drug is used in the treatment of movement disorders, seizures, or for the control of continuous involuntary movement disorders (epilepsy, Parkinson's disease, or spasticity). Examples of anti-parkinson agents include anticholinergics, dopaminergic agents, and ethosuximides. Examples of skeletal muscle relaxants include baclofen, tizanidine, and dantrolen. Examples of anticonvulsants include barbituates, hydrantoins, succinimides, oxazolidindiones, and benzodiazepines.

In another embodiment, the drug is used in the treatment or control of incontinence. Examples of drugs possibly useful in the treatment or control of incontinence include oxybutynin, tolterodine, lamotrigine and valproate.

In yet another embodiment, the drug is used in the treatment of mood and/or anxiety disorders. Examples of anti-anxiety agents include lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene.

In various embodiments, the drug molecules for release can be PEGylated, a technique known in the art to extend the in vivo lifetime of a bioactive molecule, for example by attaching the bioactive molecule to PEG or another oligomeric or polymeric stabilizing agent.

The drug can be provided as part of a "release system," as taught in U.S. Pat. No. 5,797,898, the degradation, dissolution, or diffusion properties of which can provide a method for controlling the release rate of the molecules. The release system may include one or more pharmaceutical excipients. Suitable pharmaceutically acceptable excipients include most carriers approved for parenteral administration, including various aqueous solutions. Other excipients may be used to maintain the drug in suspensions as an aid to reservoir filling, stability, or release. Depending on the properties of the drug, such excipients may be aqueous or non-aqueous, hydrophobic or hydrophilic, polar or non-polar, protic or aprotic. See. e.g., U.S. Pat. No. 6,264,990 to Knepp et al. The release system optionally includes stabilizers, antioxidants, antimicrobials, preservatives, buffering agents, surfactants, and other additives useful for storing and releasing molecules from the reservoirs in vivo.

Reservoir Caps

As used herein, the term "reservoir cap" includes a membrane or other structure suitable for separating the contents of a reservoir from the environment outside of the reservoir. It generally is self-supporting across the reservoir opening, although caps having additional structures to provide mechanical support to the cap can be fabricated. Selectively removing the reservoir cap or making it permeable will then "expose" the contents of the reservoir to the environment (or selected components thereof) surrounding the reservoir. In preferred embodiments, the reservoir cap is selectively disintegrated. As used herein, the term "disintegrate" is used broadly to include without limitation degrading, dissolving, rupturing, fracturing or some other form of mechanical failure, as well as a loss of structural integrity due to a chemical reaction (e.g., electrochemical degradation) or phase change (e.g., melting) in response to a change in temperature, unless a specific one of these mechanisms is indicated. In one specific embodiment, the "disintegration" is by an electrochemical activation technique, such as described in U.S. Pat. No. 5,797,898. In another specific embodiment, the "disintegration" is by an electro-thermal ablation technique, such as described in U.S. patent application Ser. No. 10/641,507, filed Aug. 15, 2003.

In active release devices, the reservoir cap generally includes any material that can be disintegrated or permeabilized in response to an applied stimulus, e.g., electric field or current, magnetic field, change in pH, or by thermal, chemical, electrochemical, or mechanical means.

In one embodiment, the reservoir cap is a thin metal film and is impermeable to the surrounding environment (e.g., body fluids). In one variation, a particular electric potential is applied to the metal reservoir cap, which is then oxidized and disintegrated by an electrochemical reaction, to release the drug from the reservoir. Examples of suitable reservoir cap materials include gold, silver, copper, and zinc. In another variation, the reservoir cap is heated (e.g., using a resistive heater) to cause the reservoir cap to melt and be displaced from the reservoir to open it. This latter variation could be used, for example, with reservoir caps formed of a metal or a non-metal material, e.g., a polymer. In yet another variation, the reservoir cap is formed of a polymer or other material that undergoes a temperature-dependent change in permeability such that upon heating to a pre-selected temperature, the reservoir is rendered permeable to the drug and bodily fluids to permit the drug to be released from the reservoir through the reservoir cap.

In still another embodiment, the reservoir cap is formed of a conductive material, such as a metal film, through which an electrical current can be passed to electrothermally ablate it, as described in U.S. patent application Ser. No. 10/641,507, filed Aug. 15, 2003. Representative examples of suitable reservoir cap materials include gold, copper, aluminum, silver, platinum, titanium, palladium, various alloys (e.g., Au/Si, Au/Ge, Pt—Ir, Ni—Ti, Pt—Si, SS 304, SS 316), and silicon doped with an impurity to increase electrical conductivity, as known in the art. In one embodiment, the reservoir cap is in the form of a thin metal film. In one embodiment, the reservoir cap is part of a multiple layer structure, for example, the reservoir cap can be made of multiple metal layers, such as a multi-layer/laminate structure of platinum/titanium/platinum. The reservoir cap is operably (i.e. electrically) connected to an electrical input lead and to an electrical output lead, to facilitate flow of an electrical current through the reservoir cap. When an effective amount of an electrical current is applied through the leads and reservoir cap, the temperature of the reservoir cap is locally increased due to resistive heating, and the heat generated within the reservoir cap increases the temperature sufficiently to cause the reservoir cap to be electrothermally ablated (i.e., ruptured).

In passive release devices, the reservoir cap is formed from a material or mixture of materials that degrade, dissolve, or disintegrate over time, or that do not degrade, dissolve, or disintegrate, but are permeable or become permeable to molecules or energy. Representative examples of reservoir cap materials include polymeric materials, and non-polymeric materials such as porous forms of metals, semiconductors, and ceramics. Passive semiconductor reservoir cap materials include nanoporous or microporous silicon membranes.

Characteristics can be different for each reservoir cap to provide different times of release of drug formulation. For example, any combination of polymer, degree of crosslinking, or polymer thickness can be modified to obtain a specific release time or rate.

Any combination of passive and/or active release reservoir cap can be present in a single drug delivery module. For example, the reservoir cap can be removed by electrothermal ablation to expose a passive release system that only begins its passive release after the reservoir cap has been actively removed. Alternatively, a given device can include both passive and active release reservoirs.

Means for Controlling Drug Release

The drug delivery device includes a control means to control the time at which the drug is released from the device, and into the patient's body.

In one embodiment, the means for controllably releasing the drug provides selective actuation of each reservoir, which is done under the control of a microprocessor. Preferably, such means includes an input source, a microprocessor, a timer, a demultiplexer (or multiplexer), and a power source. As used herein, the term "demultiplexer" also refers to multiplexers. The power source provides energy to activate the selected reservoir, i.e., trigger release of drug from the particular reservoir desired for a given dose. The microprocessor can be programmed to initiate the disintegration or permeabilization of the reservoir cap in response at a pre-selected time or in response to one or more of signals or measured parameters, including receipt of a signal from another device (for example by remote control or wireless methods) or detection of a particular condition using a sensor such as a biosensor.

The medical device can also be activated or powered using wireless means, for example, as described in U.S. 20020072784 A1 to Sheppard et al. The telemetry means shown in FIG. 1 can be employed in this manner, as well as to communicate instructions for or power the electrical stimulation.

In one embodiment, the medical device includes a substrate having a two-dimensional array of reservoirs arranged therein, a release system comprising drug contained in the reservoirs, anode reservoir caps covering each of the reservoirs, cathodes positioned on the substrate near the anodes, and means for actively controlling disintegration of the reservoir caps. The energy drives a reaction between selected anodes and cathodes. Upon application of a small potential between the electrodes, electrons pass from the anode to the cathode through the external circuit causing the anode material (reservoir cap) to oxidize and dissolve into the surrounding fluids, exposing the release system containing the drug for delivery to the surrounding fluids, e.g., in vivo. For example, the microprocessor can direct power to specific electrode pairs through a demultiplexer as directed by an EPROM, remote control, or biosensor.

In another embodiment, the activation energy initiates a thermally driven rupturing or permeabilization process, for example, as described in PCT WO 01/12157. For example, the means for controlling release can actively disintegrate or permeabilize a reservoir cap using a resistive heater. The resistive heater can cause the reservoir cap to undergo a phase change or fracture, for example, as a result of thermal expansion of the reservoir cap or release system, thereby rupturing the reservoir cap and releasing the drug from the selected reservoir. The application of electric current to the resistive heater can be delivered and controlled using components as described above for use in the electrochemical disintegration embodiment. For example, a microprocessor can direct current to select reservoirs at desired intervals.

In yet another embodiment, control means controls electro-thermal ablation of the reservoir cap. For example, the drug delivery device could include a reservoir cap formed of an electrically conductive material, which prevents the reservoir contents from passing out from the device; an electrical input lead connected to the reservoir cap; an electrical output lead connected to the reservoir cap; and a control means to deliver an effective amount of electrical current through the reservoir cap, via the input lead and output lead, to heat and rupture the reservoir cap to release the drug. In one embodiment, the reservoir cap and conductive leads are formed of the same material, where the temperature of the reservoir cap increases locally under applied current because the reservoir cap is suspended in a medium that is less thermally conductive than the substrate. Alternatively, the reservoir cap and conductive leads are formed of the same material, and the reservoir cap has a smaller cross-sectional area in the direction of electric current flow, where the increase in current density through the reservoir cap causes an increase in localized heating. The reservoir cap alternatively can be formed of a material that is different from the material forming the leads, wherein the material forming the reservoir cap has a different electrical resistivity, thermal diffusivity, thermal conductivity, and/or a lower melting temperature than the material forming the leads. Various combinations of these embodiments can be employed as described in U.S. patent application Ser. No. 10/641,507, filed Aug. 15, 2003.

In one embodiment, the drug delivery device utilizes an accelerated release mechanism. In one embodiment, a positive displacement feature can be included to facilitate release of the drug from the reservoirs. For example, the device may include an osmotic engine or water-swellable component, which can be used to drive a drug formulation from the reservoirs. For example, such a feature can provide very fast release of drug the efficacy of which is dependent on a fast pharmacokinetic pulsatile profile. As used herein, the term "accelerated release" refers to an increase in the transport rate of drug out of the reservoir relative to the transport rate of the drug solely by diffusion down its own chemical gradient. The terms also refer to expelling reservoir contents that would not otherwise egress from an open reservoir, i.e., where no or negligible diffusion could occur.

C. Microcontroller and Other Components

As used herein, the term "microcontroller" is used to refer to microprocessors, state machines, digital logic, or a combination thereof, which is operable to control (i) the drug delivery module, (ii) the neural electrical stimulator, (iii) the interaction of the drug delivery module and the neural electrical stimulator module, or (iv) a combination thereof.

For example, the microcontroller means controls the signal generator for the delivery of electrical stimulation to neural tissue and the control means of the drug delivery device. In one embodiment, the device includes control circuitry comprising a microprocessor, a timer, a demultiplexer, and an input source (for example, a memory source, a signal receiver, or a biosensor), telemetry communication circuit, and a power source. The timer and demultiplexer circuitry can be designed and incorporated directly onto the surface of the drug delivery device substrate during electrode fabrication, or may be incorporated in a separate integrated circuit. The criteria for selection of a microprocessor are small size, low power requirement, and the ability to translate the output from memory sources, communication signals, signal receivers, or biosensors into an address for the direction of power through the demultiplexer to a specific drug reservoir and/or the generation of an electrical signal for neural tissue stimulation (see, e.g., Ji, et al., *IEEE J. Solid-State Circuits* 27:433-43 (1992)). Selection of a source of input to the microprocessor such as memory sources, signal receivers, or biosensors depends on the medical device's particular application and whether device operation is preprogrammed, controlled by remote means, or controlled by feedback from its environment (i.e., biofeedback).

A microprocessor is used in conjunction with a source of memory (such as an erasable programmable read only memory (EPROM), an on-board flash memory, and/or an external EEPROM), a timer, a demultiplexer, and a power source such as a battery (e.g., a lithium battery). A programmed sequence of events including the time a reservoir is to be opened and the location or address of the reservoir can be stored into the memory source by the user. When the time for exposure or release has been reached as indicated by the timer, the microprocessor sends a signal corresponding to the address (location) of a particular reservoir to the demultiplexer. The demultiplexer routes an input, such as an electric potential or current, to the reservoir addressed by the microprocessor.

Sensors

In an optional embodiment, the medical device includes a sensor or sensing component. For example, the sensor or sensing component can be located in a reservoir or can be attached to the device substrate. The sensor can operably communicate with the device, e.g., through a microprocessor, to control or modify the drug release variables, including dosage amount and frequency, time of release, effective rate of release, selection of drug or drug combination, and the like. The "sensing component" includes a component utilized in measuring or analyzing the presence, absence, or change in a chemical or ionic species, energy, or one or more physical properties (e.g., pH, pressure). Types of sensors include biosensors, chemical sensors, physical sensors, or optical sensors. Further examples of such sensors and sensor components are described in PCT WO 01/64344. The sensor or sensing component detects (or not) the species or property at the site of in vivo implantation (e.g., in a bodily fluid or tissue), and further may relay a signal to the microprocessor used for controlling release from the medical device, as detailed below and herein. Such a signal could provide feedback on and/or finely control the release of drug and electrical stimulation. In one possible embodiment, the sensor could be used to sense an upcoming neural event, such as an epileptic seizure.

There are several different options for receiving and analyzing data obtained with devices located in the medical device. For example, the medical device may be controlled by local microprocessors or remote control. Biosensor information may provide input to the controller to determine the time and type of activation automatically, with human intervention, or a combination thereof. In one embodiment, the medical device includes a biosensor that can detect an oncoming of a biological event, and the device can initiate or alter the drug therapy or stimulation therapy or both provided by the medical device such that the effects of the biological event are limited or prevented.

Typically, the operation of the medical device will be controlled by an on-board (i.e., within the package) microprocessor. After analysis and processing, the output signal can be stored in a writeable computer memory chip, and/or can be sent (e.g., wirelessly) to a remote location away from the microchip. Power can be supplied locally by a battery or remotely by wireless transmission.

In one embodiment, the medical device includes one or more biosensors (which may be sealed in reservoirs until needed for use) that are capable of detecting and/or measuring signals within the body of a patient. As used herein, the term "biosensor" includes sensing devices that transduce the chemical potential of an analyte of interest into an electrical signal (e.g., an ion selective field effect transistor or ISFET), as well as electrodes that measure electrical signals directly or indirectly (e.g., by converting a mechanical or thermal energy into an electrical signal). For example, the biosensor may measure intrinsic electrical signals (electrocardiogram (ECG), electroencephalogram (EEG), evoked response, or other neural signals), pressure, temperature, pH, or loads on tissue structures at various in vivo locations. The electrical signal from the biosensor can then be measured, for example by a microprocessor/controller, which then can transmit the information to a remote controller, another local controller, or both. For example, the system can be used to relay or record information on the patient's vital signs or the implant environment, such as drug concentration.

Packaging

The medical devices described herein will typically be packaged into a hermetically sealed package, e.g., in a titanium encasement, which essentially exposes only the reservoir caps and stimulation electrodes. These microelectronic device packages are typically made of an insulating or dielectric material such as aluminum oxide or silicon nitride. Low cost packages can also be made of ceramics, plastics, or reinforced epoxies. The package serves to allow all components of the device to be placed in close proximity and to facilitate the interconnection of components to power sources and to each other, while protecting the electronics from the environment.

In one embodiment, the device comprises an outer layer comprising a single layer or a multi-layer/laminate structure that includes combinations of silicon oxide ($SiO_x$), silicon nitride ($SiN_x$) or silicon carbide ($SiC_x$). In one embodiment, photoresist is patterned on top of the dielectric to protect it from etching except on the reservoir caps covering each reservoir. The dielectric material can be etched by physical or chemical etching techniques. The purpose of this film is to protect the reservoir caps and leads from corrosion, degradation, delamination, or dissolution in all areas where they do not have to be exposed to the surrounding environment, to shield electrically active components from the in vivo environment, and to enhance the biostability of the device materials.

Methods of Making the Devices

The devices and modules described herein can be made using techniques known in the art and/or described herein. Certain methods are described in U.S. Pat. No. 5,797,898; U.S. Pat. No. 6,123,861; U.S. patent application Publication No. 2002/0107470; and U.S. patent application Publication No. 2002/0151776, which are hereby incorporated by reference in their entirety. One skilled in the art can fabricate, or obtain the components and assemble them into, the medical devices described herein. The assembly of a complete medical device may involve a number of packaging steps which can include (1) attachment of electrical leads to a microchip drug delivery device, (2) filling of the reservoirs with a release system comprising drug, (3) sealing the reservoirs, (4) integration with electronic components and power sources and electrodes, and (5) placing the drug delivery module and associated components within a single enclosure or "package."

Operation and Use of the Devices

A number of treatment regiments utilizing electrical stimulation and drug therapy can be employed for a vast array of physiological disorders or pathological conditions associated with the sympathetic and parasympathetic nervous system. Physiological disorders that may be treated include hyperhydrosis, complex regional pain syndrome and other pain syndromes such as headaches, cluster headaches, abnormal cardiac sympathetic output, cardiac contractility, excessive blushing condition, hypertension, renal disease, heart failure, angina, hypertension, and intestinal motility disorders, dry eye or mouth disorders, sexual dysfunction, asthma, liver disorders, pancreas disorders, and heart disorders, pulmonary disorders, gastrointestinal disorders, and billatory disorders. The number of disorders to be treated is limited only by the number, variety, and placement of electrodes (or combinations of multiple electrodes) along the sympathetic nervous system. In one embodiment, complications can be largely minimized, or possibly eliminated, by the use of chronic or intermittent electrical stimulation and/or sensing aberrant neuronal signaling continuous or intermittent drug infusion. The reasons are many, and include the possibility of changing which contacts of a multipolar lead are stimulated to minimize stimulating a portion of the ganglion. Adjusting parameters, such as frequency, pulse amplitude, and/or pulse width, of the electronic stimulation should also minimize adverse consequences and increase beneficiary effects.

In many instances, the preferred effect is to stimulate or reversibly block nervous tissue. Use of the term "block" or "blockade" in this application means disruption, modulation, and inhibition of nerve impulse transmission. Abnormal regulation can result in an excitation of the pathways or a loss of inhibition of the pathways, with the net result being an increased perception or response. Therapeutic measures can be directed towards either blocking the transmission of signals or stimulating inhibitory feedback. Electrical stimulation permits such stimulation of the target neural structures and, equally importantly, prevents the total destruction of the nervous system. Additionally, electrical stimulation parameters can be adjusted so that benefits are maximized and side effects are minimized.

In one embodiment of an active-release embodiment, the medical device can be controlled by a pre-programmed microprocessor to open one or a portion of the reservoirs intermittently (that is, a different one or more reservoirs after predetermined time intervals) to effect release intermittently, e.g., in a pulsatile manner. In other variations, the microprocessor (and thus release) is controlled by a sensor, e.g., a biosensor, or by remote control. The microprocessor also coordinates and controls delivery of the electrical signals to the electrodes connected to the neural tissue to be stimulated.

Further details on methods of using microchip devices for controlled release of drug are described in U.S. Pat. No. 5,797,898 and No. 6,123,861; and PCT WO 02/30401, WO 02/30264, WO 01/91902, WO 01/64344, WO 01/41736, WO 01/35928, and WO 01/12157.

In one embodiment, the drug delivery module is for subcutaneous drug delivery, to release drugs into the subcutaneous region which then diffuse into regional tissue or into body fluid-containing structures, including, for example, the cardiovascular system, the lymphatic system, the respiratory system, the digestive system, the central nervous system (cerebral spinal fluid), the genitourinary system, or the eyes. With the device, a drug can be administered to treat one or more of these tissues or structures or fluids within the structures, or can be transported through these tissues or structures to distal treatment locations or to cellular binding sites.

In another embodiment, the drug delivery module provides direct communication between the source of the drug (e.g., a reservoir) and the particular fluid-containing structure of interest, so that when drug is released, it enters the fluid without contacting the subcutaneous region. This could be useful, for example, for administrating a drug that if released in the subcutaneous space would cause inflammation, irritation, other tissue injury/dysfunction, or would diffuse too slowly into a fluid-containing structure to achieve an effective concentration in the fluid (e.g., because of clearance mechanisms). For example, the device could directly release a therapeutic agent into one or more body cavities or tissue lumens, including an intrathecal space, an intracranial space, an abdominal/peritoneal space, a thoracic space, an intrapericardial space, a renal space, or a hepatic space. For example, the substrate could have a shape that is compatible with the fluid-containing structure, such as tubular to reside within a blood vessel (e.g., intravascular), rounded and buoyant to float in the bladder, or curved to conform to the eye. The control circuitry and power needed to activate the reservoir caps can be located in a control module outside or inside of the fluid-containing structure. If the control module is located external to the fluid-containing structure, electrical conductors can be used to connect to the reservoir caps.

Figure 5:
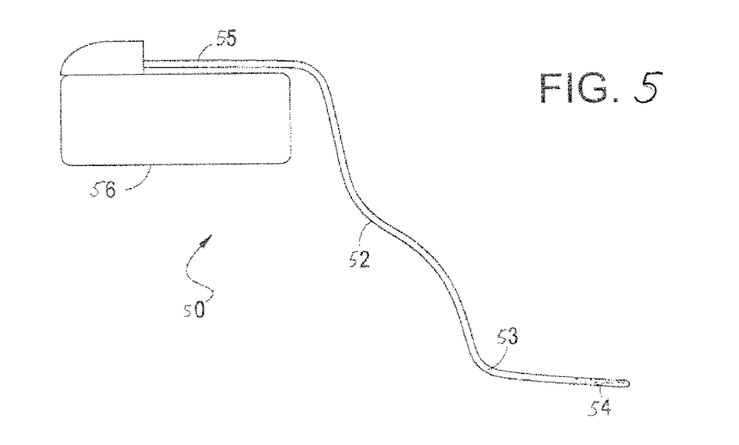
FIG. 5 is a perspective view of one embodiment of an implantable medical device that includes a catheter having drug-containing reservoirs at the distal end portion.
Figure 6A:
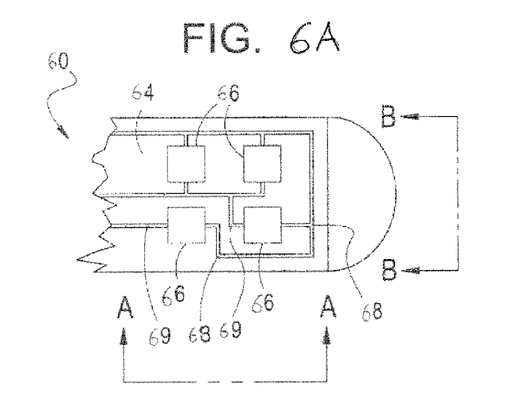
FIG. 6A is a plan view of one embodiment of the distal end portion of a catheter having an array of drug-containing reservoirs covered by reservoir caps that can be activated/opened using electrothermal ablation as described herein.
Figure 6B:
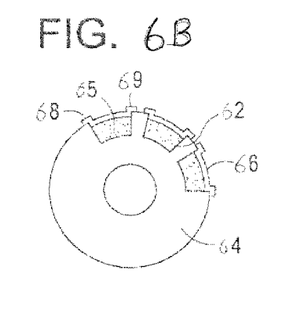
FIG. 6B is a cross-sectional view of the device shown in FIG. 6A, taken along line B/B.
Figure 6C:
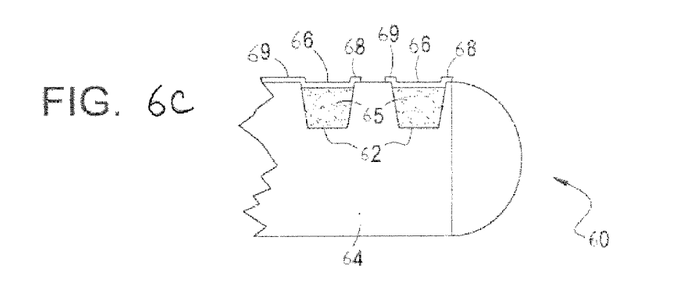
FIG. 6C is a cross-section view of the device, taken along line C/C.

In one embodiment, a drug delivery module includes a catheter which can be inserted into the tissue lumen or structure of interest and which has one or more drug-containing reservoirs fabricated therein, for example at a distal portion of the catheter. FIG. 5 illustrates one embodiment of a medical device 50 which includes a catheter 52 which can be inserted into the tissue lumen or structure of interest and which has one or more drug-containing reservoirs 54 fabricated therein, for example at a distal portion 53 of the catheter. The body of the catheter serves as the substrate in which the reservoirs are fabricated, for example using soft lithography or other techniques known in the art. For example, tens or hundreds of micro-reservoirs could be arrayed around the catheter body at the distal tip portion. The reservoirs are hermetically sealed by conductive reservoir caps, which are electrically connected to a power source and can be disintegrated by electrothermal ablation as described herein. Advantageously, the power source and control hardware 56 can be located at a proximal end of the catheter 55 so they need not fit into or be located at the delivery site. The electrical traces could be built into the catheter body or supported on an inner or outer surface of the catheter body. FIGS. 6A-C illustrates a catheter tip portion 60 which has reservoirs 62 is substrate/catheter body 64, wherein the reservoirs contain therapeutic agent 65 and are covered by conductive reservoir caps 66, each of which are connected to input and output electrical leads 68 and 69, respectively. See U.S. Patent Application No. 2002/0111601, which disclosed another embodiment of a catheter type implantable medical device, one that utilizes a different reservoir opening technology than the electrothermal ablation system described herein.

Optionally, the catheter can have an internal fluid passageway extending between a proximal end portion and a distal end portion. The fluid passageway can be in communication with an infusion pump and a reservoir (e.g., a refillable reservoir containing a therapeutic fluid), so that the device can deliver a therapeutic fluid through the passageway to the delivery site. In one embodiment, the pump is placed abdominally in a subcutaneous pocket, and the catheter is inserted into the intrathecal space of the spine, tunneled under the skin and connected to the pump. Such an embodiment could be used, for example, in the management of chronic pain or for spasticity therapy. The microarray of drug-containing reservoirs can be provided (i) on or in the body of the catheter, (ii) in a substrate device that is located at the proximal end of the catheter and releases drug into an infusion fluid pumped across the microarray openings to form a fluid/drug mixture that is pumped through the fluid passageway of the catheter, or (iii) in a combination of these. In one embodiment, the distal tip portion of the catheter includes one or more biological sensors to detect patient conditions that indicate the desirability or need for drug release. The sensors could extend from or be on the surface of the tip portion of the catheter body or could be located within one or more reservoirs. In one version, the device could include one catheter having a sensor on the distal end portion for implantation at a first she in vivo, and a second catheter having drug-containing reservoirs on the distal end portion for implantation at a second site in vivo.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A medical device for electrical stimulation of neural tissue and controlled drug delivery comprising:
    an implantable drug delivery module which comprises
        a substrate having a plurality of reservoirs,
        a release system contained in each of the reservoirs, wherein the release system comprises at least one drug,
        a plurality of discrete reservoir caps, each being in register with an opening of one of the reservoirs, separating the release system from an environment outside of the reservoirs, and
        means for disintegrating one or more of the reservoir caps by electrothermal ablation to release the at least one drug from one or more of the reservoirs;
    a neural electrical stimulator which comprises
        a signal generator, and
        at least one stimulation electrode for operable engagement with a neural tissue of a patient, wherein the at least one stimulation electrode is connected to the signal generator; and
    at least one microcontroller for controlling operational interaction of the drug delivery module and the neural electrical stimulator.

2. The medical device of claim 1, wherein the at least one microcontroller controls both the signal generator and the means for disintegrating one or more of the reservoir caps of the drug delivery module.

3. The medical device of claim 1, further comprising a power source operably connected to the means for disintegrating one or more of the reservoir caps, the neural electrical stimulator, the at least one microcontroller, or a combination thereof.

4. The medical device of claim 1, wherein the stimulation electrode is on an outer surface of a hermetically sealed encasement containing the drug delivery module and microcontroller.

5. The medical device of claim 1, further comprising a hermetically sealed encasement containing the drug delivery module and microcontroller, wherein the stimulation electrode extends a distance from the hermetically sealed encasement.

6. The medical device of claim 5, wherein a flexible catheter connects the stimulation electrode to the encasement.

7. The medical device of claim 1, further comprising telemetry components in operable communication with the microcontroller.

8. The medical device of claim 1, wherein the neural electrical stimulator is provided as a module separate from the drug delivery module.

9. The medical device of claim 8, wherein the neural electrical stimulator module is implantable.

10. The medical device of claim 8, wherein the drug delivery module is controlled by a telemetry or hard-wired signal from the stimulator module.

11. The medical device of claim 8, comprising two microcontrollers, one of which controls the stimulator module and the other which controls the drug delivery module.

12. The medical device of claim 1, adapted to treat chronic pain in a patient.

13. The medical device of claim 1, adapted to treat a movement disorder in a patient.

14. The medical device of claim 1, adapted to treat incontinence in a patient.

15. The medical device of claim 1, adapted to treat obesity in a patient.

16. The medical device of claim 1, adapted to control seizures in a patient.

17. The medical device of claim 1, wherein the drug delivery module comprises a microchip drug delivery device.

18. The medical device of claim 1, further comprising one or more sensors operable to deliver a signal to the microcontroller.

19. The medical device of claim 18, wherein the one or more sensors control release of the drug from the drug delivery module and control generation of an electrical current from the neural stimulator to neural tissue.

20. The medical device of claim 1, wherein the drug is an analgesic, an anti-anxiety agent, an anti-incontinence agent, a skeletal muscle relaxant, an anti-convulsant, or an anti-parkinson agent.

21. The medical device of claim 1, wherein the implantable drug delivery module comprises a catheter or tube, the plurality of reservoirs being located proximate to an end of the catheter or tube.

22. The medical device of claim 1, wherein the substrate comprises silicon and the discrete reservoir cap comprises at least one metal film.

23. The medical device of claim 22, wherein the discrete reservoir cap comprises a multi-layer structure comprising platinum and titanium.

24. A method of treating a patient comprising delivery of an electrical signal and at least one drug to a patient in need thereof comprising:
   implanting into the patient a device comprising a drug delivery module which comprises a plurality of discrete reservoirs, each containing a drug, and a plurality of discrete reservoir caps, each in register with an opening of one of the reservoirs;
   bringing an stimulator electrode into operable engagement with a neural tissue of the patient;
   activating a signal generator to deliver electrical stimulation from the stimulator electrode to the neural tissue of the patient; and
   passing an electric current though one or more of the discrete reservoir caps to disintegrate the one or more discrete reservoir caps by electrothermal ablation, thereby to release the drug from one or more of the reservoirs into the patient.

25. The method of claim 24, wherein the drug and the electrical neural stimulation are delivered simultaneously.

26. The method of claim 24, wherein the drug is delivered intermittently or continuously.

27. The method of claim 24, wherein the electrical stimulation is delivered intermittently or continuously.

28. The method of claim 24, wherein the drug is released before the electrical neural stimulation and is effective to reduce the stimulation threshold of the neural tissue.

29. The method of claim 24, wherein release of the drug is alternated with the delivery of the electrical stimulation.

30. The method of claim 24, wherein the neural electrical stimulator is provided as a module separate from the drug delivery module.

31. The method of claim 30, further comprising implanting the neural electrical stimulator into the patient.

32. The method of claim 24, which is used to treat chronic pain in the patient.

33. The method of claim 24, which is used to treat a movement disorder in the patient.

34. The method of claim 24, which is used to treat incontinence in the patient.

35. The method of claim 24, which is used to treat obesity in the patient.

36. The method of claim 24, which is used to control seizures in the patient.

37. The method of claim 24, wherein the device further comprises at least one microcontroller for controlling operational interaction of the drug delivery module and the neural electrical stimulator.

* * * * *

UNITED STATES PATENT AND TRADEMARK OFFICE
CERTIFICATE OF CORRECTION

| | | |
|---|---|---|
| PATENT NO. | : 7,599,737 B2 | Page 1 of 1 |
| APPLICATION NO. | : 10/679763 | |
| DATED | : October 6, 2009 | |
| INVENTOR(S) | : Yomtov et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 404 days.

Signed and Sealed this

Twenty-eighth Day of September, 2010

David J. Kappos
*Director of the United States Patent and Trademark Office*